United States Patent [19]

Kawakami et al.

[11] 4,039,583

[45] Aug. 2, 1977

[54] PROCESS FOR PRODUCING METHACROLEIN

[75] Inventors: Masato Kawakami, Yokohama; Naoki Andoh; Akira Iio, both of Yokkaichi, all of Japan

[73] Assignee: Japan Synthetic Rubber Co., Ltd., Tokyo, Japan

[21] Appl. No.: 636,887

[22] Filed: Dec. 2, 1975

[30] Foreign Application Priority Data

Dec. 6, 1974 Japan .................. 49-139448

[51] Int. Cl.² ............. C07C 45/04; C07C 5/00
[52] U.S. Cl. ................. 260/604 R; 260/680 E
[58] Field of Search ........... 260/604 R, 666 A, 680 E; 252/470

[56] References Cited

U.S. PATENT DOCUMENTS

| 3,387,038 | 6/1968 | Koch | 260/604 R |
|---|---|---|---|
| 3,624,146 | 11/1971 | Parthasarthy | 260/533 N |
| 3,786,000 | 1/1974 | Ono et al. | 252/464 |
| 3,836,586 | 9/1974 | Yamada et al. | 260/604 R |
| 3,894,091 | 7/1975 | Sakakibara et al. | 260/604 R |

Primary Examiner—James O. Thomas, Jr.
Assistant Examiner—W. B. Lone
Attorney, Agent, or Firm—Ladas, Parry, Von Gehr, Goldsmith & Deschamps

[57] ABSTRACT

In a process for producing methacrolein by the gas phase catalytic reaction of isobutene with molecular oxygen in the presence of a catalyst consisting of Mo, Bi, Fe, Co, Sb and O, the catalyst is prepared by using as the Sb component, a mixture of a trivalent Sb compound and a pentavalent Sb compound. When said catalyst is used, the reaction can be continued over a long period of time without formation of complete oxidation products, i.e. CO and $CO_2$, and, even when the starting isobutene contains n-butene, the reaction proceeds smoothly to make it possible to produce methacrolein and 1,3-butadiene simultaneously.

14 Claims, No Drawings

PROCESS FOR PRODUCING METHACROLEIN

This invention relates to a process for producing methacrolein either alone or simultaneously with 1,3-butadiene by the gas phase catalytic oxidation of isobutene or a hydrocarbon mixture composed mainly of isobutene and $C_4$ aliphatic hydrocarbons including butene-1, and cis- and trans-butene-2 (the said mixture will be abbreviated to "the butene mixture", hereinafter) in the presence of a novel catalyst which is particularly long in catalyst life.

Heretofore, many multi-component system catalysts have been proposed as catalysts for the gas phase catalytic oxidation of olefinic hydrocarbons (refer to, for example, Japanese patent publication Nos. 2324/68, 11733/72, 32042/72, 11964/72, 4762/73 and 33930/71). When viewed from the practical industrial standpoint, however, all these catalysts are still insufficient in conversion, selectivity and one-pass yield, and particularly in catalyst life.

The present inventors found that a multi-component system catalyst consisting of Mo, Bi, Fe, Co, Sb and O is markedly excellent in conversion, selectivity and one-pass yield and thus can successfully be used as a catalyst for the gas phase catalytic oxidation of isobutene or the butene mixture, and have already applied for a patent on the said catalyst (U.S. patent application Ser. NO. 468,044). In this catalyst, the effect or Sb was so marked as to increase the conversion of isobutene and the selectivity for methacrolein and to decrease the selectivity for complete oxidation products, as compared with the case of a catalyst containing no Sb. From the industrial standpoint, however, the said catalyst also was not sufficiently satisfactory.

The present inventors have further conducted studies on the said specific effect of antimony to find an unexpected effect of antimony which cannot be thought of from the conventional oridinary chemical knowledge. Heretofore, it has been considered that when an antimony compound is calcined, whether the antimony in the antimony compound is trivalent or pentavalent, the final product is an oxide of antimony with a stoichiometric ratio of one antimony to two oxygen atoms. Therefore, it has been considered that the valency of antimony in the antimony compound as a starting material for catalyst is not so important (see Encyclopedia of Chemical Technology, 2nd Edition, Vol. 2, p. 564). Unexpectedly, however, the present inventors have found that a catalyst consisting of Mo, Bi, Fe, Co, Sb and O, which is prepared by using as the Sb source at the time of preparation of the catalyst a mixture comprising a trivalent antimony compound and a pentavlent antimony compound, is not only long in life but also more excellent in conversion, selectivity and one-pass yield than a catalyst consisting of Mo, Bi, Fe, Co, Sb and O, in which only a trivalent or pentavalent antimony compound is used. It has also been found that in the case of the catalyst consisting of Mo, Bi, Fe, Co, Sb and O, which is prepared by use of only either or a trivalent or pentavalent antimony compound, the amounts of formed complete oxidation products such as CO and $CO_2$ increase with the lapse of reaction time, as in the case of the conventional catalyst for catalytic oxidation of olefins, whereas in the case of the catalyst consisting of Mo, Bi, Fe, Co, Sb and O, in which a mixture of a trivalent antimony compound and a pentavalent antimony compound is used according to the present invention, the amounts of formed complete oxidation products such as CO and $CO_2$ scarcely increase even after the reaction is effected over a long period of time, and thus the catalyst according to the present invention is quite preferable also from the standpoint of removal of heat at the time when the reaction is effected on an industrial scale.

When the catalyst according to the present invention is used, the starting material is not always required to be pure isobutene, and methacrolein can successfully be produced simultaneously with 1,3-butadiene, which is a useful chemical intermediate, even when there is used, for example, a spent $C_4$ fraction after extraction of butadiene, i.e. a fraction composed mainly of a mixture of butene-1, cis-butene-2, trans-butene-2 and isobutene.

An object of the present invention is to provide a catalyst for the oxidation of isobutene.

Another object of the present invention is to provide a process for producing methacrolein by oxidizing isobutene in the presence of the above-mentioned catalyst.

Other objects and advantages of the invention will become apparent from the following description.

In accordance with the present invention, there is provided a process for producing methacrolein by the gas phase catalytic oxidation of isobutene with molecular oxygen in the presence of catalyst consisting of Mo, Bi, Fe, Co, Sb and O, characterized in that catalyst in prepared by using, as the Sb component, a mixture of a trivalent Sb compound and a pentavalent Sb compound. The present invention further provides a process for producing methacrolein simultaneouly with 1,3-butadiene by the gas phase catalytic oxidation of a butene mixture containing isobutene and n-butene with molecular oxygen in the presence of the above-mentioned catalyst.

The compounds which may be used in the preparation of the catalyst used in the present invention include salts such as nitrates, carbonates, ammonium salts and halides; free acids; acid anhydrides; polyacids: hydroxides; heteropolyacids; and heteropolyacid salts of the elements to be contained in the catalyst.

Concrete examples of the compounds are as follows:

Mo: Ammonium molybdate, molybdenum trioxide, molybdic acid, sodium molybdate, potassium molybdate, phosphomolybdic acid, ammonium phosphomolybdate, etc.

Bi: Bismuth nitrate, bismuth oxide, etc.

Fe: Iron nitrate, iron oxide, etc.

Co: Cobalt nitrate, cobalt oxide, cobalt hydroxide, etc.

In the present invention, the trivalent Sb source to be used is not particularly limited so far as the antimony is in a trivalent state at the time of mixing of catalyst components, and may ordinarily be any of diantimony trioxide, antimony trichloride, antimony tribromide, antimony (III) oxychloride, antimony (III) pentoxydichloride, antimony (III) sulfide and the like which are easily available. Further, the pentavalent Sb source to be used is not particularly limited so far as the antimony is in a pentavalent state at the time of mixing of catalyst components, and may ordinarily be any of diantimony pentoxide, antimony pentachloride, antimony (V) sulfide and the like which are easily available.

The composition of the catalyst used in the present invention is such that the atomic ratio of Mo : Bi : Fe : Co : Sb is 10 : (0.1–8) : (0.1–10) : (0.1–20) : (0.01–5), preferably 10 : (0.5–5) : (1–10) : (1–15) : (0.1–3). The proportion of oxygen in the catalyst is a value defined by the valences of other individual elements, and is ordinarily a numerical value of 35 to 90. This composition of the catalyst has been clarified by the studies of the present inventors, and the details thereof are disclosed in U.S. patent application Ser. No. 468,044. The atomic ratio of Sb (III/Sb (V) in the starting material is preferably 0.1/0.9 to 0.95/0.05, more preferably 0.5/0.5 to 0.9/0.1. In the preparation of the catalyst, the use of trivalent antimony is necessary for maintaining the activity of catalyst, and the use of pentavalent antimony is effective for inhibiting the formation of complete oxidation products such as CO, $CO_2$, etc. Although it is necessary that in all the Sb components, the pentavalent Sb component is present in an amount of 5 mole % or more, preferably 10 mole % or more, the use of an excess thereof results in deterioration of activity of catalyst and in reduction of conversion. Therefore, it is used in a proportion of 90 mole % or less, preferably 50 mole % or less.

The catalyst of the present invention may be prepared in such a known manner as evaporation to dryness or mixing of oxides, and it is also possible to substantially reduce the amount of the catalyst by use of a carrier. As the carrier, there may be used any of silica, alumina, silicon carbide, pumice, etc. Among these, however, silicon carbide or alumina is preferable. It is desirable to take such a procedure that after molding the catalyst components or adhering them onto the carrier, the resulting catalyst is calcined at such a high temperature as 400° to 800° C. and then used in the reaction.

The space velocity at the time of reaction may be 1,000 to 5,000 hr$^{-1}$ (NTP basis), but is preferably 1,500 to 4,000 hr$^{-1}$.

The molar ratio of isobutene to molecular oxygen in the feed starting gas to be introduced into the reaction system may be in the range of 1 : ( : 0.5-5). The practice, however, the reaction can successfully be carried out in such a low oxygen ratio as about 1 : (1-3). The conventional catalyst has been relatively short in catalyst life under reaction conditions of low oxygen ratio, whereas the catalyst of the present invention is extremely long in catalyst life even under such conditions, and thus the reaction can be effected with high efficiency.

Further, butanes and 1,3-butadiene have no great influence on the reaction conditions, so that even if there is any change in composition of the starting material, the desired reaction can be accomplished by changing the operational conditions. Furthermore, in this reaction, the reaction gas may be diluted with an inert gas having no adverse effect on the reaction, for example, nitrogen, steam, carbon dioxide or saturated hydrocarbon. Particularly, steam has the action to sustain the catalyst activity, so that the use thereof is advantageous for the reaction of the present invention. However, it is not desirable to dilute the reaction gas excessively, since the yield per unit time is lowered. When steam is used, the molar ratio of isobutene to steam is usually 1 : (0.3-100), preferably 1 : (0.5-30).

The reaction is carried out at a temperature of 350° to 550° C., preferably 370° to 500°C. Sufficiently good results can be obtained when the reaction is effected at atmospheric pressure.

Since no essential difference in effectiveness is brought about due to the difference in particle size of the catalyst, any of a fixed bed or fluidized bed type reactor may be used in the reaction.

The reaction products can be recovered and separated by a conventional procedure, e.g. by condensation, extraction or distillation.

The present invention is illustrated in detail below with reference to examples, in which the conversion of n-butene ($n-C_4^=$) or isobutene ($i-C_4^=$), the selectivity for 1,3-butadiene (BD), methacrolein (MAcr) or methacrylic acid (MAA), and the yield are defined by the following formulas;

Conversion (mole %) =

$$\frac{\text{Moles of consumed n-butene (or isobutene)}}{\text{Moles of fed n-butene (or isobutene)}} \times 100$$

Selectivity (mole %) =

$$\frac{\text{Moles of formed 1,3-butadiene (or formed methacrolein or methacrylic acid)}}{\text{Moles of consumed n-butene (or isobutene)}} \times 100$$

Yield (mole %) =
Conversion (mole %) $\times$ Selctivity (mole %) $\times$ 1/100

EXAMPLE 1

To an aqueous solution containing 22.10 g. (17.86 mmol.) of ammonium molybdate was added an aqueous solution containing 25.44 g. (87.6 mmol.) of cobalt nitrate. To this mixed solution were added with thorough stirring an aqueous, hydrochloric acid-acidified solution containing 2.30 g. (10.00 mmol.) of antimony trichloride, and 0.404 g. (1.25 mmol.) of a diantimony pentoxide powder. Further, an aqueous solution containing 12.62 g. (31.2 mmol.) of ferric nitrate, and an aqueous, nitric acid-acidified solution containing 2.04 g. (12.50 mmol.) of bismuth nitrate were successively added with stirring, and the resulting mixture was evaporated to dryness. The resulting residue was thermally decomposed at 250° C. for 4 hours, and then pulverized in a mortar. To 20 g. of the resulting power were added 30 g. of granular silicon carbide (grain size 3 mm.) and 100 cc. of distilled water, and the resulting mixture was evaporated to dryness with stirring to adhere the catalyst components to the carrier. The resulting residue was calcined at 650° C. for 5 hours to prepare a catalyst. The atomic ratio of the individual metals in the catalyst components was Mo : Bi : Fe : Co : Sb = 10 : 1 : 2.5 : 7 : 1, and the antimony atomic ratio of the starting trivalent antimony compound to the starting pentavalent antimony compound was 1 : 0.25.

8.3 Cubic centimeters of the thus prepared catalyst was packed in a quartz reactor tube having an inner diameter of 20 mm., and was brought into contact with a starting gas consisting of 67 mole % of air, 22.5 mole % of steam and 10.5 mole % of a hydrocarbon mixture, which contained 27.7 mole % of butene-1, 4.2 mole % of cis-butene-2, 8.2 mole % of trans-butene-2, 47.5 mole % of isobutene, 9.9 mole % of butenes, 1.0 mole % of 1,3-butadiene and 1.5 mole % of $C_3$ hydrocarbons, at a space velocity of 3,000 hr$^{-1}$ (0° C., 1 atm.). The reaction temperature (the maximum temperature in the catalyst layer) was 450° C. The results obtained after 6 hours and 2,000 hours from initiation of the reaction were as shown in Table 1. Even after the reaction had been continuously effected for 2,000 hours, the catalyst was scarcely lowered in activity.

COMPARATIVE EXAMPLE 1

A catalyst was prepared in the same manner as in Example 1, except that an aqueous, hydrochloric acid-acidified solution containing 2.86 g. (12.50 mmol.) of antimony trichloride was used in place of the aqueous, hydrochloric acid-acidified solution containing 2.30 g. (10.00 mmol.) of antimony trichloride, and 0.404 g. (1.25 mmol.) of the diantimony pentoxide powder. The atomic ratio of the individual metals in the catalyst components was Mo : Bi : Fe : Co : Sb = 10 : 1 : 2.5 : 7 : 1. Using the thus prepared catalyst, the same reaction as in Example 1 was effected. The results obtained after 6 hours and 2,000 hours from initiation of the reaction was as shown in Table 1. After the reaction had been continuously effected for 2,000 hours, the catalyst used in this example was far more lowered in activity than the catalyst used in Example 1.

COMPARATIVE EXAMPLE 2

A catalyst was prepared in the same manner as in Example 1, except that 2.02 g. (6.25 mmol.) of a diantimony pentoxide powder was used in place of the aqueous, hydrochloric acid-acidified solution containing 2.30 g. (10.00 mmol.) of antimony trichloride, and 0.404 g. (1.25 mmol.) of the diantimony pentoxide powder. The atomic ratio of the individual metals in the catalyst components was Mo : Bi : Fe : Co : Sb = 10 : 1 : 2.5 : 7 : 1. Using the thus prepared catalyst, the same reaction as in Example 1 was effected. The results obtained after 6 hours and 300 hours from initiation of the reaction were as shown in Table 1. The catalyst used in this example was lower in activity than that used in Example 1.

EXAMPLE 2

A catalyst was prepared in the same manner as in Example 1, except that 1.46 g. (5.0 mmol.) of a diantimony trioxide powder was used in place of the aqueous hydrochloric acid-acidified solution containing 2.30 g. (10.00 mmol.) of antimony trichloride, 30 g. of granular alumina (grain size 3 mm.) was used in place of 30 g. of the granular silicon carbide (grain size 3 mm.), and the calcination temperature was varied to 700° C. The atomic ratio of the individual metals in the catalyst components was Mo : Bi : Fe : Co : Sb = 10 : 1 : 2.5 : 7 : 1, and the atomic ratio of the starting trivalent antimony to the starting pentavalent antimony was 1 : 0.25. Using the thus prepared catalyst, the same reaction as in Example 1 was effected. The results obtained after 6 hours and 2,000 hours from initiation of the reaction were as shown in Table 1. Even after the reaction had been effected for 2,000 hours, catalyst was scarcely lowered in activity.

EXAMPLE 3

Using the catalyst prepared in Example 2, the same reaction as in Example 1 was effected, except that the starting gas was replaced by a mixture comprising 8.5 mol % of isobutene, 68.5 mole % of air and 23.0 mole % of steam. The results obtained after 6 hours and 2,000 hours from initiation of the reaction were as shown in Table 1. Even after the reaction had been effected for 2,000 hours, the catalyst was scarcely lowered in activity.

EXAMPLE 4

A catalyst was prepared in the same manner as in Example 1, except that 35.43 g. (87.6 mmol.) of ferric nitrate was used in place of 12.62 g. (31.2 mmol.) of the ferric nitrate, and the calcination temperature was varied to 700° C. The atomic ratio of the individual metals in the catalyst components was Mo : Bi : Fe : Co : Sb = 10 : 1 : 7 : 7 : 1, and the antimony atomic ratio of the starting trivalent antimony to the starting pentavalent antimony was 1 : 0.25. Using the thus prepared catalyst, the same reaction as in Example 1 was effected. The results obtained after 6 hours and 1,000 hours from initiation of the reaction were as shown in Table 1. Even after the reaction had been effected for 1,000 hours, the catalyst was scarcely lowered in activity.

EXAMPLE 5

A catalyst was prepared in the same manner as in Example 1, except that 0.748 g. (2.50 mmol.) of antimony peptachloride was used in place of 0.404 g. (1.25 mmol.) of the diantimony pentoxide powder, and the calcination temperature was varied to 700° C. The atomic ratio of the individual metals in the catalyst components was Mo : Bi : Fe : Co : Sb = 10 : 1 : 2.5 : 7 : 1, and the antimony atomic ratio of the starting trivalent antimony compound to the starting pentavalent antimony compound was 1 : 0.25. Using the thus prepared catalyst, the same reaction as in Example 1 was effected. The results obtained after 6 hours and 1,000 hours from initiation of the reaction were as shown in Table 1. Even after the reaction had been effected for 1,000 hours, the catalyst was scarcely lowered in activity.

EXAMPLE 6

A catalyst was prepared in the same manner as in Example 1, except that the antimony trichloride was used in an amount of 2.71 g. (11.9 mmol.), the diantimony pentoxide was used in an amount of 0.101 g. (0.31 mmol.), and the calcination temperature was varied to 700° C. The atomic ratio of the individual metals in the catalyst components was Mo : Bi : Fe : Co : Sb — 10 : 1 : 2.5 : 7 : 1, and the antimony atomic ratio of the starting trivalent antimony compound to the starting pentavalent antimony compound was 1 : 0.053. Using the thus prepared catalyst, the same reaction as in Example 1 was effected. The results obtained after 6 hours and 1,000 hours from initiation of the reaction were as shown in Table 1. Even after the reaction had been effected for 1,000 hours, the catalyst was scarcely lowered in activity.

EXAMPLE 7

A catalyst was prepared in the same manner as in Example 1, excpet that the antimony trichloride was used in an amount of 0.285 g. (1.25 mmol.), and the diantimony pentoxide was used in an amount of 1.82 g. (5.63 mmol.). The atomic ratio of the individual metals in the catalyst components was Mo : Bi : Fe : Co : Sb = 10 : 1 : 1 : 2.5 : 7 : 1, and the antimony atomic ratio of the starting trivalent antimony compound to the starting pentavalent antimony compound was 1 : 9. Using the thus prepared catalyst, the same reaction as in Example 1 was effected. The results obtained after 6 hours, 1,000 hours and 2,000 hours from initiation of the reaction was as shown in Table 1.

EXAMPLE 8

The same procedure as in Example 1 was repeated, except that 1.74 g (10.00 mmol.) of antimony oxychloride and 0.404 g (1.25 mmol.) of diantimony pentoxide were used. The atomic ratio of the individual metals in the catalyst components was Mo : Bi : Fe : Co : Sb = 10 : 1 : 2.5 : 7 : 1, and the atomic ratio of the trivalent anitomoy compound to the pentavalent antimony compound used in the preparation of the catalyst was 1 : 0.25.

used in an amount of 1.150 g. (5.00 mmol.) and the diantimony pentoixide was used in an amount of 1.212 g. (3.75 mmol.). The atomic ratio of the individual metals in the catalyst components was Mo : Bi : Fe : CO : Sb = 10 : 1 : 2.5 : 7 : 1, and the antimony atomic ratio of the starting trivalent antimony compound to the starting pentavalent antimony compound was 1 : 1.5. Using the thus prepared catalyst, the same reaction as in Example 1 was effected. The results obtained after 6 hours, 1,000 hours and 2,000 hours from initiation of the reaction were as shown in Table 1.

Table 1

| Example No. | Catalyst | Sb source Trivalent antimony compound | Sb source Pentavalent antimony compound | Reaction time (hr.) |
|---|---|---|---|---|
| Example 1 | $Mo_{10}Bi_1Fe_{2.5}Co_7Sb_1$ | $SbCl_3$ ($Sb_{0.8}$) | $Sb_2O_5$ ($Sb_{0.2}$) | 6 / 2000 |
| Comparative Example 1 | $Mo_{10}Bi_1Fe_{2.5}Co_7Sb_1$ | $SbCl_3$ ($Sb_1$) | (—) | 6 / 2000 |
| Comparative Example 2 | $Mo_{10}Bi_1Fe_{2.5}Co_7Sb_1$ | (—) | $Sb_2O_5$ ($Sb_1$) | 6 / 300 |
| Example 2 | $Mo_{10}Bi_1Fe_{2.5}Co_7Sb_1$ | $Sb_2O_3$ ($Sb_{0.8}$) | $Sb_2O_5$ ($Sb_{0.2}$) | 6 / 2000 |
| Example 3 | $Mo_{10}Bi_1Fe_{2.5}Co_7Sb_1$ | $Sb_2O_3$ ($Sb_{0.8}$) | $Sb_2O_5$ ($Sb_{0.2}$) | 6 / 2000 |

| Conversion (mole %) | | Selectivity (mole %) | | | | Yield (mole %) | | |
|---|---|---|---|---|---|---|---|---|
| i-$C_4^=$ | n-$C_4^=$ | MAcr | MAA | BD | CO + $CO_2^*$ | MAcr | MAA | BD |
| 94.0 | 63.5 | 75.1 | 2.0 | 93.0 | 8.0 | 70.6 | 1.9 | 59.1 |
| 93.5 | 60.3 | 74.2 | 2.1 | 91.5 | 8.6 | 69.4 | 2.0 | 55.2 |
| 93.0 | 65.0 | 73.5 | 1.1 | 93.0 | 8.0 | 68.4 | 1.0 | 60.5 |
| 84.4 | 49.9 | 69.2 | 1.6 | 93.0 | 12.0 | 58.4 | 1.4 | 46.4 |
| 65.0 | 23.6 | 83.7 | 0.74 | 98.1 | 6.1 | 54.4 | 0.5 | 23.1 |
| 63.9 | 23.0 | 80.9 | 0.70 | 98.8 | 6.3 | 51.7 | 0.5 | 22.7 |
| 97.1 | 72.6 | 75.7 | 2.3 | 91.1 | 8.2 | 73.6 | 2.2 | 66.1 |
| 95.8 | 70.1 | 76.7 | 2.2 | 93.2 | 8.3 | 73.5 | 2.1 | 65.3 |
| 95.0 | — | 77.1 | 2.6 | — | 11.8 | 73.2 | 2.5 | — |
| 94.2 | — | 77.0 | 2.6 | — | 12.2 | 72.5 | 2.4 | — |

| Example 4 | $Mo_{10}Bi_1Fe_7Co_7Sb_1$ | $SbCl_3$ ($Sb_{0.8}$) | $Sb_2O_5$ ($Sb_{0.2}$) | 6 / 1000 |
|---|---|---|---|---|
| Example 5 | $Mo_{10}Bi_1Fe_{2.5}Co_7Sb_1$ | $SbCl_3$ ($Sb_{0.8}$) | $SbCl_5$ ($Sb_{0.2}$) | 6 / 1000 |
| Example 6 | $Mo_{10}Bi_1Fe_{2.5}Co_7Sb_1$ | $SbCl_3$ ($Sb_{0.95}$) | $Sb_2O_5$ ($Sb_{0.05}$) | 6 / 1000 |
| Example 7 | $Mo_{10}Bi_1Fe_{2.5}Co_7Sb_1$ | $SbCl_3$ ($Sb_{0.1}$) | $Sb_2O_5$ ($Sb_{0.9}$) | 6 / 1000 / 2000 |
| Example 8 | $Mo_{10}Bi_1Fe_{2.5}Co_7Sb_1$ | SbOCl ($Sb_{0.8}$) | $Sb_2O_5$ ($Sb_{0.2}$) | 6 / 1000 |

| 98.7 | 75.4 | 72.3 | 2.8 | 90.1 | 9.8 | 71.4 | 2.8 | 67.9 |
| 98.0 | 73.3 | 72.8 | 2.7 | 92.1 | 9.8 | 71.3 | 2.6 | 67.5 |
| 97.4 | 70.3 | 70.3 | 2.4 | 91.1 | 8.1 | 68.5 | 2.3 | 64.0 |
| 96.9 | 69.1 | 70.5 | 2.2 | 92.0 | 8.0 | 68.3 | 2.1 | 63.6 |
| 95.2 | 70.3 | 72.2 | 2.0 | 91.3 | 8.3 | 68.7 | 1.9 | 64.2 |
| 94.5 | 68.0 | 72.2 | 1.9 | 92.2 | 9.0 | 68.2 | 1.8 | 62.7 |
| 83.7 | 53.3 | 81.0 | 0.89 | 96.6 | 6.6 | 67.8 | 0.7 | 51.5 |
| 82.1 | 50.6 | 81.2 | 0.79 | 96.8 | 6.3 | 66.7 | 0.7 | 49.0 |
| 80.8 | 48.5 | 81.1 | 0.80 | 96.5 | 6.5 | 65.5 | 0.7 | 46.8 |
| 92.8 | 63.0 | 74.5 | 2.3 | 94.5 | 8.0 | 69.1 | 2.1 | 59.5 |
| 92.5 | 61.0 | 75.0 | 2.3 | 95.0 | 8.0 | 69.4 | 2.1 | 58.0 |

| Example 9 | $Mo_{10}Bi_1Fe_{2.5}Co_7Sb_1$ | $SbCl_3$ ($Sb_{0.4}$) | $Sb_2O_5$ ($Sb_{0.6}$) | 6 / 1000 / 2000 |
|---|---|---|---|---|

| 87.0 | 54.6 | 77.5 | 1.0 | 94.5 | 7.5 | 67.4 | 0.9 | 51.6 |
| 86.5 | 52.2 | 76.5 | 1.0 | 94.0 | 7.5 | 66.2 | 0.9 | 49.1 |
| 85.3 | 50.8 | 77.0 | 1.0 | 94.5 | 7.6 | 65.7 | 0.9 | 48.1 |

Note
*Selectivity (Co + $CO_2$) =

$$\frac{\text{Moles of formed (CO + CO}_2\text{)}}{\text{Moles of consumed (i} - C_4^= \text{ or total } C_4^=)} \times \frac{100}{4}$$

The results obtained after 6 hours and 1,000 hours from the initiation of the reaction were as shown in Table 1. Even after the reaction had been effected for 1,000 hours, the catalyst activity was scarcely lowered.

EXAMPLE 9

A catalyst was prepared in the same manner as in Example 1, except that the antimony trichloride was

What is claimed is:

1. A process for producing methacrolein, or methacrolein and 1,3-butadiene, by the gas phase catalytic reaction of isobutene, or isobutene and n-butene, with molecular oxygen or a molecular oxygen-containing gas in the presence of a catalyst having a composition of the formula, $$Mo_{10}Bi_{0.1-8}Fe_{0.1-10}Co_{0.01-20}Sb_{0.01-5}O_n$$

wherein $n$ is a number defined by the valences of the respective catalyst component elements said number being from 35 to 90, at a temperature of 350° to 550° C., characterized in that the catalyst is prepared by using, as the Sb component, a mixture of a trivalent Sb compound and a pentavalent Sb compound in an antimony atomic ratio of the former to the latter of 0.1/0.9 to 0.95/0.05, wherein the trivalent Sb compound is selected form the group consisting of diantimony trioxide, antimony trichloride, antimony tribromide, antimony (III) oxychloride and antimony (III) pentoxydichloride, and the pentavalent Sb compound is selected from the group consisting of diantimony pentoxide, antimony pentachloride and antimony (v) sulfide.

2. A process according to claim 1, wherein the catalyst has a composition of the formula, $$Mo_{10}Bi_{0.5-5}Fe_{1-10}Co_{1-15}Sb_{0.1-3}O_n$$

wherein $n$ is from 35 to 75.

3. A process according to claim 1, wherein the antimony atomic ratio of the trivalent Sb compound to the pentavalent Sb compound used at the time of preparation of the catalyst is in the range of Sb (III)/Sb (V) = 0.5/0.5 − 0.9/0.1.

4. A process according to claim 1, wherein the trivalent Sb compound is diantimony trioxide or antimony trichloride, and the pentavalent Sb compound is diantimony pentoxide or antimony pentachloride.

5. A process according to claim 1, wherein methacrolein is produced by using isobutene as the starting material.

6. A process according to claim 1, wherein methacrolein and 1,3-butadiene are produced by using isobutene and n-butene as the starting materials.

7. A process according to claim 1, wherein the molecular oxygen-containing gas is air.

8. A process according to claim 1, wherein the gas phase catalytic reaction is effected in the presence of an inert gas.

9. A process according to claim 8, wherein the inert gas is steam.

10. A process according to claim 9, wherein the ratio of isobutene to steam is 1 : 0.3–100.

11. A process according to claim 9, wherein the ratio of isobutene to steam is 1 : 0.5–30.

12. A process according to claim 1, wherein the gas phase catalytic reaction is effected at a temperature in the range from 370° to 500° C.

13. A process according to claim 1, wherein the ratio of isobutene to molecular oxygen is 1 : 0.5–5.

14. A process according to claim 1, wherein the ratio of isobutene to molecular oxygen is 1 : 1–3.

* * * * *